(12) United States Patent
Chronister et al.

(10) Patent No.: US 8,777,616 B2
(45) Date of Patent: Jul. 15, 2014

(54) CORDLESS DENTAL HANDPIECE, SYSTEM INCLUDING A CORDLESS DENTAL HANDPIECE, AND METHOD OF CONNECTING A CORDLESS DENTAL HANDPIECE

(75) Inventors: Benjamin Chronister, Parkesburg, PA (US); Jeremy Kile, York, PA (US); Eugene J. Novak, Deerfield, IL (US)

(73) Assignee: DENTSPLY International Inc., York, PA (US)

( * ) Notice: Subject to any disclaimer, the term of this patent is extended or adjusted under 35 U.S.C. 154(b) by 0 days.

(21) Appl. No.: 12/896,332

(22) Filed: Oct. 1, 2010

(65) Prior Publication Data

US 2011/0081624 A1    Apr. 7, 2011

Related U.S. Application Data

(60) Provisional application No. 61/248,097, filed on Oct. 2, 2009.

(51) Int. Cl.
*A61C 1/08* (2006.01)

(52) U.S. Cl.
USPC .......................................... 433/126; 433/125

(58) Field of Classification Search
USPC ................. 433/114, 124, 126, 146, 115–123, 433/127–133, 141, 142, 153, 125; 285/321, 285/398, 415; 403/9, 109.3, 365; 292/256.6–256.65
See application file for complete search history.

(56) References Cited

U.S. PATENT DOCUMENTS

| 4,315,744 | A | * | 2/1982 | Albert ........................... 433/126 |
|---|---|---|---|---|
| 4,706,367 | A | * | 11/1987 | Garringer .................. 29/525.05 |
| 5,057,015 | A | * | 10/1991 | Fleer .............................. 433/126 |
| 5,219,285 | A | * | 6/1993 | Meller et al. .................. 433/126 |
| 5,655,906 | A | * | 8/1997 | Coss et al. ..................... 433/115 |
| 5,749,728 | A | * | 5/1998 | Bailey ........................... 433/125 |
| 7,422,432 | B2 | | 9/2008 | Warner |
| 7,439,463 | B2 | | 10/2008 | Brenner et al. |
| D595,851 | S | | 7/2009 | Karten et al. |
| 2003/0232305 | A1 | | 12/2003 | Warner |
| 2004/0115591 | A1 | | 6/2004 | Warner |
| 2005/0046185 | A1 | * | 3/2005 | Olson .......................... 285/321 |
| 2005/0130097 | A1 | | 6/2005 | Warner |
| 2005/0130098 | A1 | | 6/2005 | Warner |
| 2005/0214712 | A1 | * | 9/2005 | Shaygan ....................... 433/125 |
| 2006/0024642 | A1 | | 2/2006 | Stadeker |
| 2006/0184092 | A1 | | 8/2006 | Atanasoska et al. |
| 2006/0210948 | A1 | | 9/2006 | Rose et al. |
| 2007/0030166 | A1 | | 2/2007 | Warner et al. |
| 2007/0031780 | A1 | | 2/2007 | Warner et al. |
| 2007/0031781 | A1 | | 2/2007 | Warner et al. |
| 2007/0031782 | A1 | | 2/2007 | Warner et al. |
| 2007/0166661 | A1 | | 7/2007 | Brenner et al. |

(Continued)

FOREIGN PATENT DOCUMENTS

WO     2005053561 A2    6/2005

*Primary Examiner* — Cris L Rodriguez
*Assistant Examiner* — Matthew Seward
(74) *Attorney, Agent, or Firm* — Leana Levin; Douglas J. Hura; David A. Zdurne

(57) ABSTRACT

A cordless dental handpiece, a system including a cordless dental handpiece, and a method of connecting a cordless dental handpiece are disclosed. The cordless dental handpiece includes a first module and a second module. The second module is configured to detachably engage the first module. The second module includes a battery compartment.

17 Claims, 6 Drawing Sheets

(56) References Cited

U.S. PATENT DOCUMENTS

| | | |
|---|---|---|
| 2007/0254261 A1 | 11/2007 | Rosenblood et al. |
| 2008/0064007 A1 | 3/2008 | Carron et al. |
| 2008/0166685 A1 | 7/2008 | Rosenblood et al. |
| 2008/0262412 A1 | 10/2008 | Atanasoska et al. |
| 2009/0081610 A1* | 3/2009 | Hayman et al. ............... 433/125 |

* cited by examiner

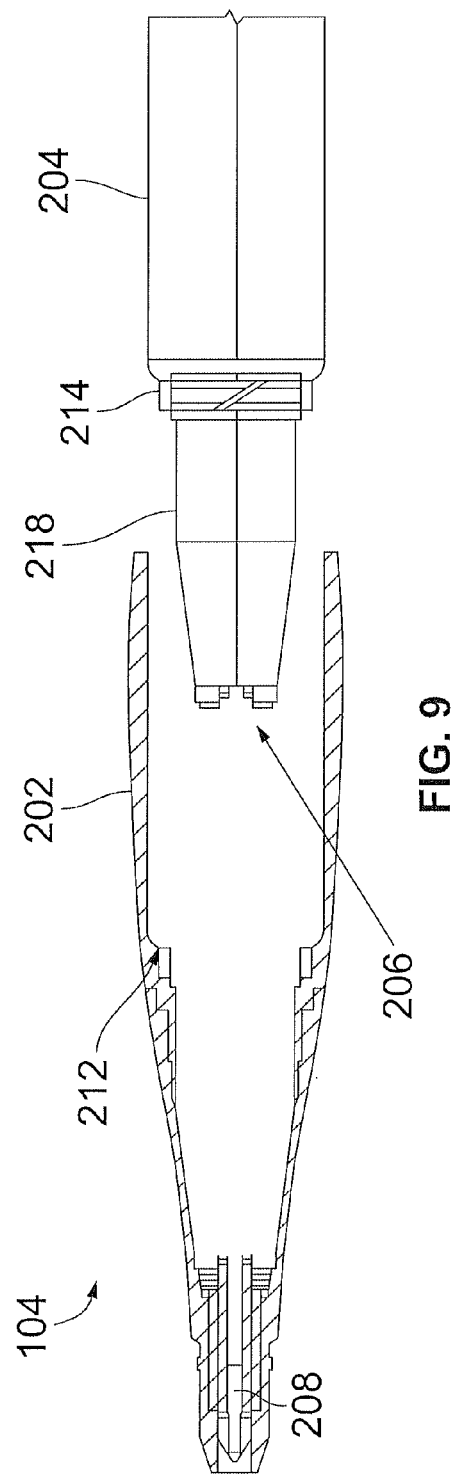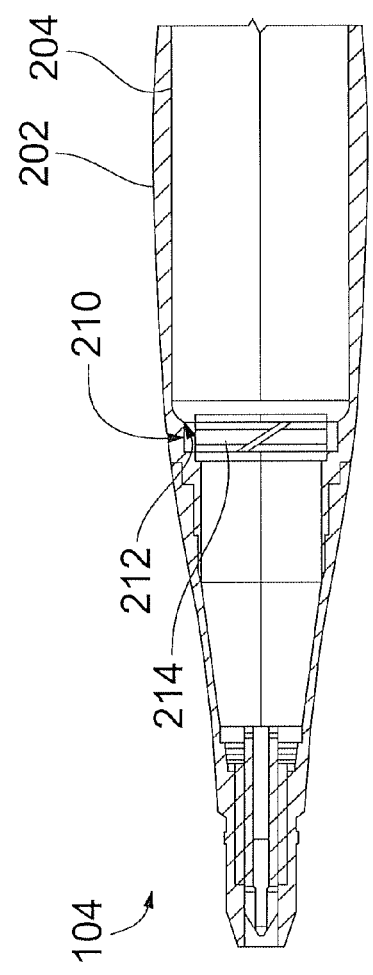
FIG. 9
FIG. 10

CORDLESS DENTAL HANDPIECE, SYSTEM INCLUDING A CORDLESS DENTAL HANDPIECE, AND METHOD OF CONNECTING A CORDLESS DENTAL HANDPIECE

PRIORITY

This application claims priority to and benefit of U.S. Pat. Provisional Application No. 61/248,097, filed Oct. 2, 2009, and titled "Dental Handpiece Connection," which is hereby incorporated by reference in its entirety.

FIELD OF THE DISCLOSURE

The present disclosure is directed to instruments used for teeth. More particularly, the disclosure relates to cordless modular dental instruments having a handpiece interchangeable with a dental tool.

BACKGROUND OF THE DISCLOSURE

Generally, dental hygiene instruments are exposed to undesirable substances including, but not limited to, plaque, blood, saliva, and/or paste. Sterilizing and/or disinfecting dental hygiene instruments can result in down-time for clinicians. To reduce or eliminate down-time, clinicians can purchase additional dental hygiene instruments. However, the purchase of additional dental hygiene instruments can result in undesirable and high costs.

Additionally or alternatively, clinicians can utilize a protective sleeve on the dental hygiene instrument. The protective sleeve can become dislodged, can undesirably add bulk to the dental hygiene instrument, can create waste, or some combination thereof. In addition, a protective sleeve may add additional cost to utilizing the dental hygiene instrument. Attaching a protective sleeve to a handpiece does not prevent wear associated with engagement and disengagement. If the wear harms the handpiece, then the technician is unable to use it.

Being capable of manipulating dental hygiene instruments is also important. Cords on dental hygiene instruments can restrict movement by the clinician. Using batteries can permit additional mobility for the clinician. However, including a battery in the dental hygiene instrument can add substantial weight, can add substantial cost, can eliminate safety concerns due to the proximity of an electrical power source to a patient, and combinations thereof.

What is needed is a dental hygiene instrument, a system including a dental hygiene instrument, and a process of connecting a dental hygiene instrument that does not suffer from the above drawbacks.

SUMMARY OF THE INVENTION

According to an embodiment of the present invention, a cordless dental handpiece includes a first module that includes a first drive that is configured to detachably engage a dental tool and a second module configured to detachably engage the first module, the second module comprising a battery compartment. The first module of the cordless dental handpiece is further configured to detachably engage the dental tool.

According to another embodiment of the present invention, a dental hygiene system includes a dental prophylaxis angle and a cordless dental handpiece. The cordless dental handpiece includes a first module that includes a first drive that is configured to detachably engage the dental prophylaxis angle and a second module configured to detachably engage the first module, the second module comprising a battery compartment. The first module of the cordless dental handpiece is further configured to detachably engage the dental prophylaxis angle.

According to yet another embodiment of the present invention, a method of connecting a cordless dental handpiece includes providing a cordless dental handpiece, detachably engaging a first module with a second module of the cordless dental handpiece, and detachably engaging the first module with a dental prophylaxis angle. The first module includes a first drive configured to detachably engage the dental prophylaxis angle and the second module comprising a battery compartment.

An advantage of a cordless dental handpiece according to an embodiment of the present invention includes a reduction or elimination of down-time for clinicians due to the modularity of the dental hygiene instrument.

Another advantage of a cordless dental handpiece according to an embodiment of the present invention includes protecting the handpiece from exposure to bodily fluids.

Another advantage of a cordless dental handpiece according to an embodiment of the present invention includes maintaining a low amount of bulk in a dental hygiene instrument by having modularity in the dental hygiene instrument.

Another advantage of a cordless dental handpiece according to an embodiment of the present invention includes permitting a modular portion having an electrical power source to be utilized with a variety of other modular portions of the dental hygiene instrument.

Another advantage of a cordless dental handpiece according to an embodiment of the present invention is that the usable life of the more expensive portions of the handpiece can be extended by reducing or eliminating wear associated with engagement and disengagement of moving parts that may be exposed to bodily fluids.

Further aspects of the method and system are disclosed herein. The features as discussed above, as well as other features and advantages of the present disclosure will be appreciated and understood by those skilled in the art from the following detailed description and drawings.

BRIEF DESCRIPTION OF THE DRAWINGS

FIG. 9 shows a sectioned view of a first module separate from a second module according to an embodiment of the disclosure.

FIG. 10 shows a sectioned view of a detachably engaged dental handpiece according to an embodiment of the disclosure.

Wherever possible, the same reference numbers will be used throughout the drawings to represent the same parts.

The present disclosure now will be described more fully hereinafter with reference to the accompanying drawings, in which an exemplary embodiment of the disclosure is shown.

This disclosure may, however, be embodied in many different forms and should not be construed as limited to the embodiments set forth herein.

DETAILED DESCRIPTION OF THE DISCLOSURE

Provided is a dental handpiece, a dental hygiene system, and a process of connecting a dental handpiece embodiments of which do not suffer from the above drawbacks. According to an exemplary embodiment of the disclosure, a dental handpiece includes a first module and a second module. The first module of the dental handpiece is configured to detachably engage a dental tool such as a dental prophylaxis angle. The second module is configured to detachably engage the first module. The second module includes a battery compartment.

Figure 3:
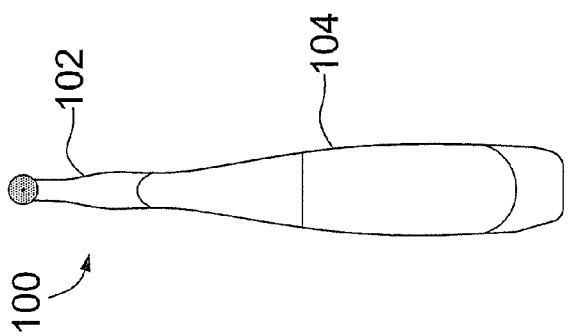
FIGS. 1-7 show alternate views of a dental hygiene system according to an embodiment of the disclosure.
Figure 2:
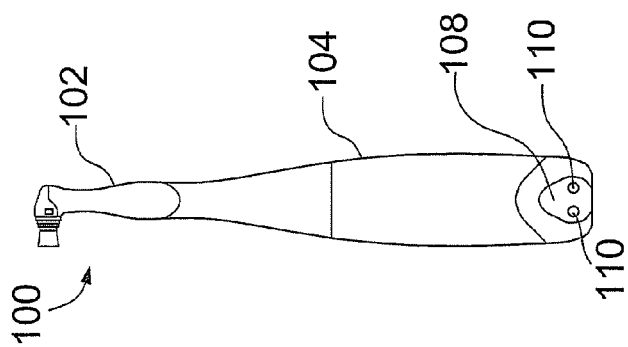
Figure 1:
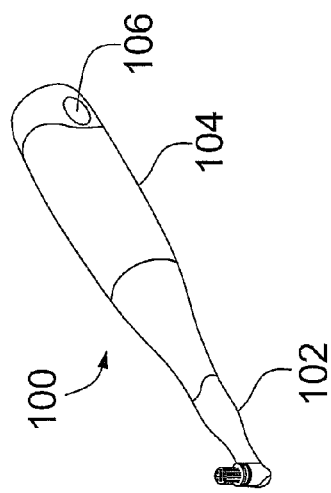
Figure 1A:
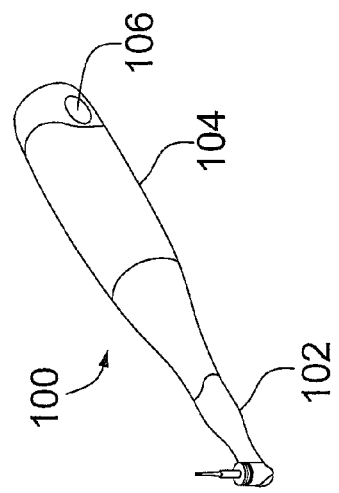
Figure 6:
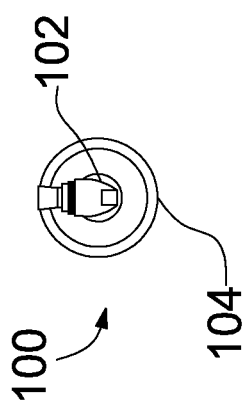
Figure 7:
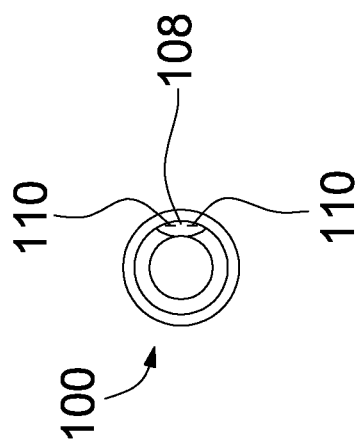
Figure 5:
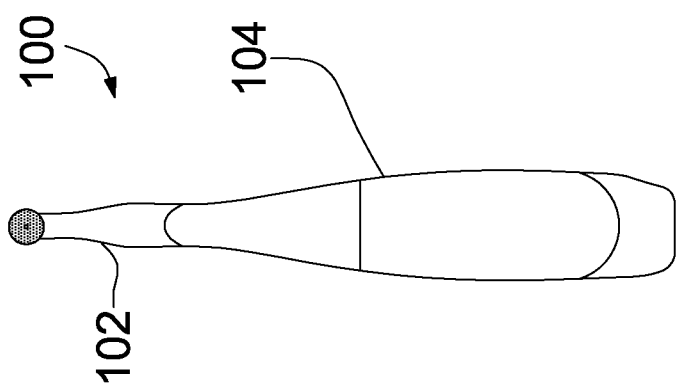
Figure 4:
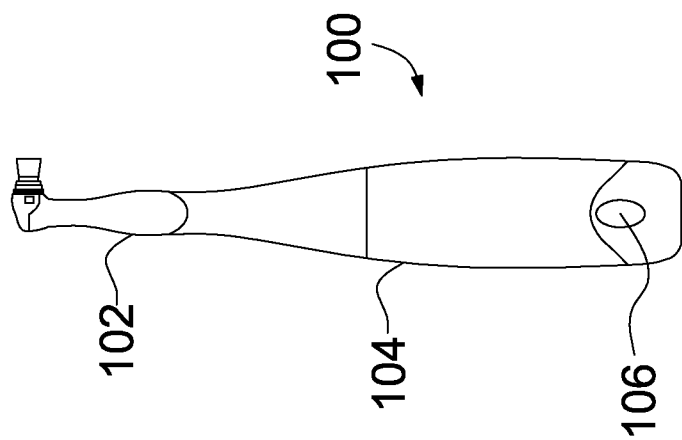

The modularity of the dental handpiece provides several advantages. The separation of the modules can protect the handpiece or portions of the handpiece from exposure to bodily fluids. The enclosing of one module around another can prevent bodily fluids from contacting an electrical power source in the battery compartment of the handpiece. The detachability of the modules can reduce bulk by maintaining a low amount of bulk (for example, an amount of bulk that allows comfortable gripping of the handpiece for a long period of time) despite including the battery compartment by enclosing the battery compartment upon the engagement of the first module and the second module. Also, the detachability can permit a modular portion including the electrical power source to be utilized with a variety of other modular portions of the dental hygiene instrument, thereby providing customization for a clinician or substantially continuous use of the modular portion including the electrical power source. Furthermore, the modular portions of the dental handpiece can be used in conjunction with one or more other dental tools including, but not limited to, the dental prophylaxis angle, a dental bur (FIG. 1A), a dental brush, or other suitable rotatable devices.

The detachability between the first module and the second module can reduce or eliminate down-time for clinicians by permitting the second module to be used with a plurality of modules similar to or identical to the first module. For example, modularity can permit additional removable portions of dental hygiene instruments to be purchased. While the removable portions are being sterilized, the remaining portions can be utilized with one of the additional removable portions. In the past, utilizing modular dental hygiene instruments has been disfavored because it can create additional surfaces and/or regions permitting undesirable substances to be deposited on the dental hygiene instrument. Utilizing the second module having the battery compartment permits elimination of a cord and, thus, permits such interfaces to be positioned at a desirable distance distal from the patient without undesirably adding to the bulk of the dental hygiene instrument.

FIGS. 1-7 show alternate views of a dental hygiene system 100 according to an exemplary embodiment of the disclosure. System 100 includes a dental prophylaxis angle (DPA) 102 and a dental handpiece 104. DPA 102 can be any DPA including, but not limited to, the DPA disclosed in U.S. patent application Ser. No. 12/004,145, assigned to the assignees of the present invention, which is hereby incorporated by reference in its entirety. Dental handpiece 104 can detachably engage DPA 102. Dental handpiece 104 can include any suitable features.

In one embodiment, dental handpiece 104 includes an indicator 106 (for example, an LED display). Indicator 106 can be used for displaying information. For example, indicator 106 can indicate a mode of use, a speed, a level of charge, status (on/off/charging/charged), any other suitable information, or any combination thereof.

Additionally or alternatively, dental handpiece 104 can include a power interface 108. Power interface 108 electrically connects a battery (not shown) housed in a battery compartment (not shown) within dental handpiece 104 to a power source (not shown). In one embodiment, power interface 108 includes one or more contacts 110 permitting electrical communication between the power source and the battery compartment, the battery, or both. System 100 can have smooth transitions and/or tight tolerances between DPA 102, dental handpiece 104, indicator 106, power interface 108, and/or contacts 110. In one embodiment, the one or more contacts 110 can contact one or more mating contacts (not shown) on a charging station (not shown) when the dental handpiece 104 is engaged. In another embodiment, the one or more contacts 110 can contact one or more mating contacts on a charging station upon modules of the dental handpiece 104 being detached. Stated another way, in this embodiment, the one or more contacts 110 are enclosed by the dental handpiece 104 and exposed upon detaching modules from the dental handpiece 104.

Figure 8:
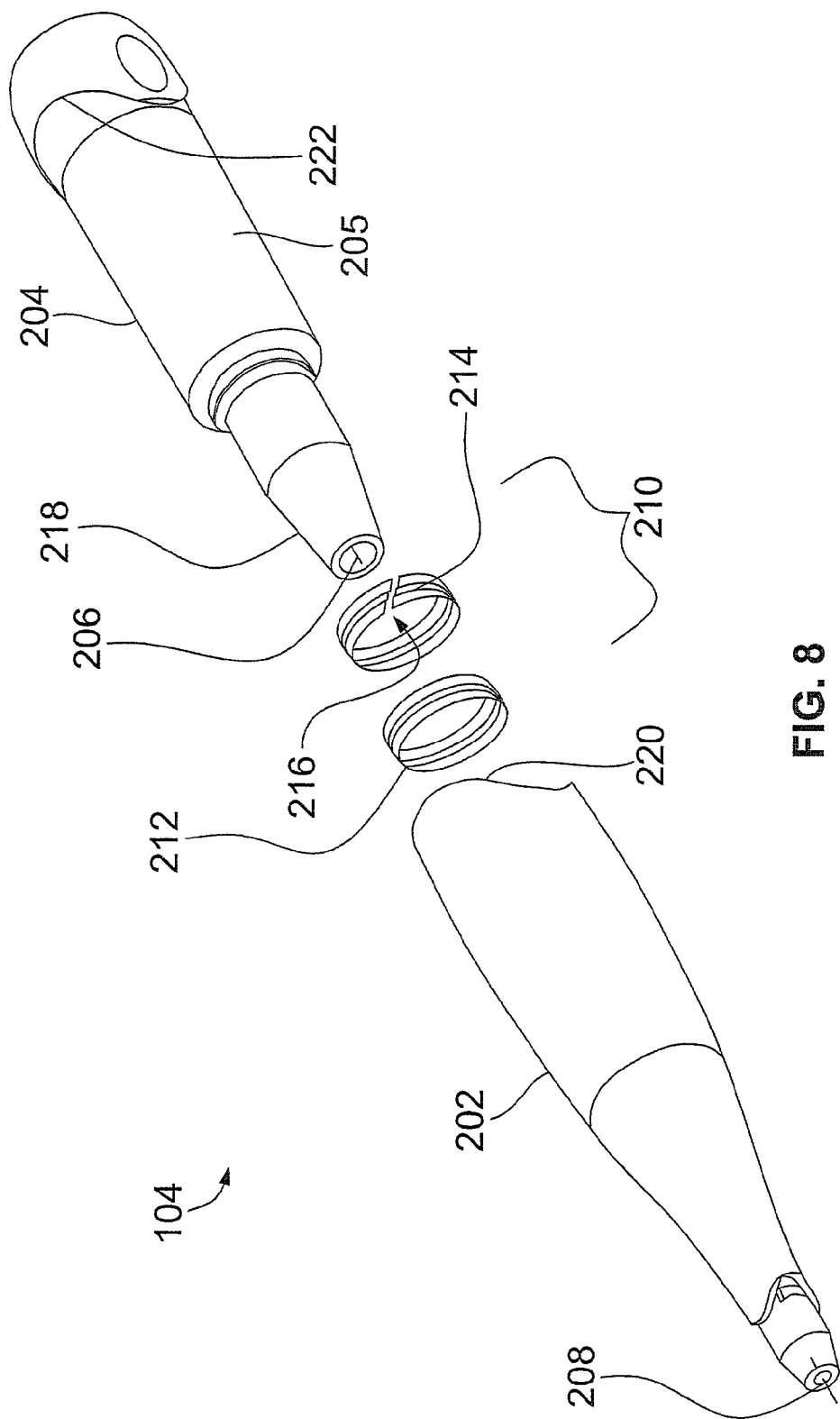
FIG. 8 shows a dental handpiece according to an embodiment of the disclosure.
Figure 11:
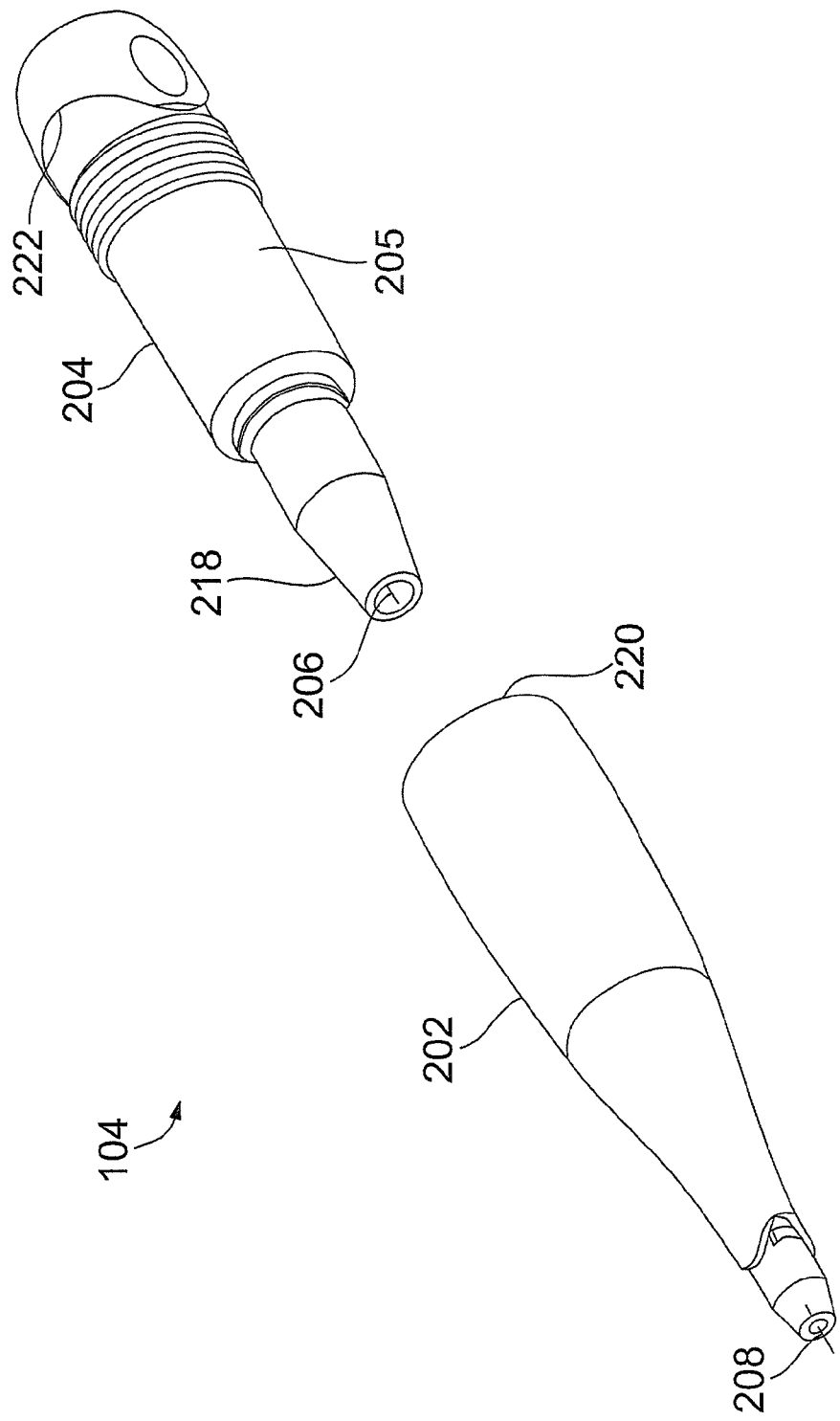
FIG. 11 shows a dental handpiece according to one embodiment of the disclosure.
Figure 12:
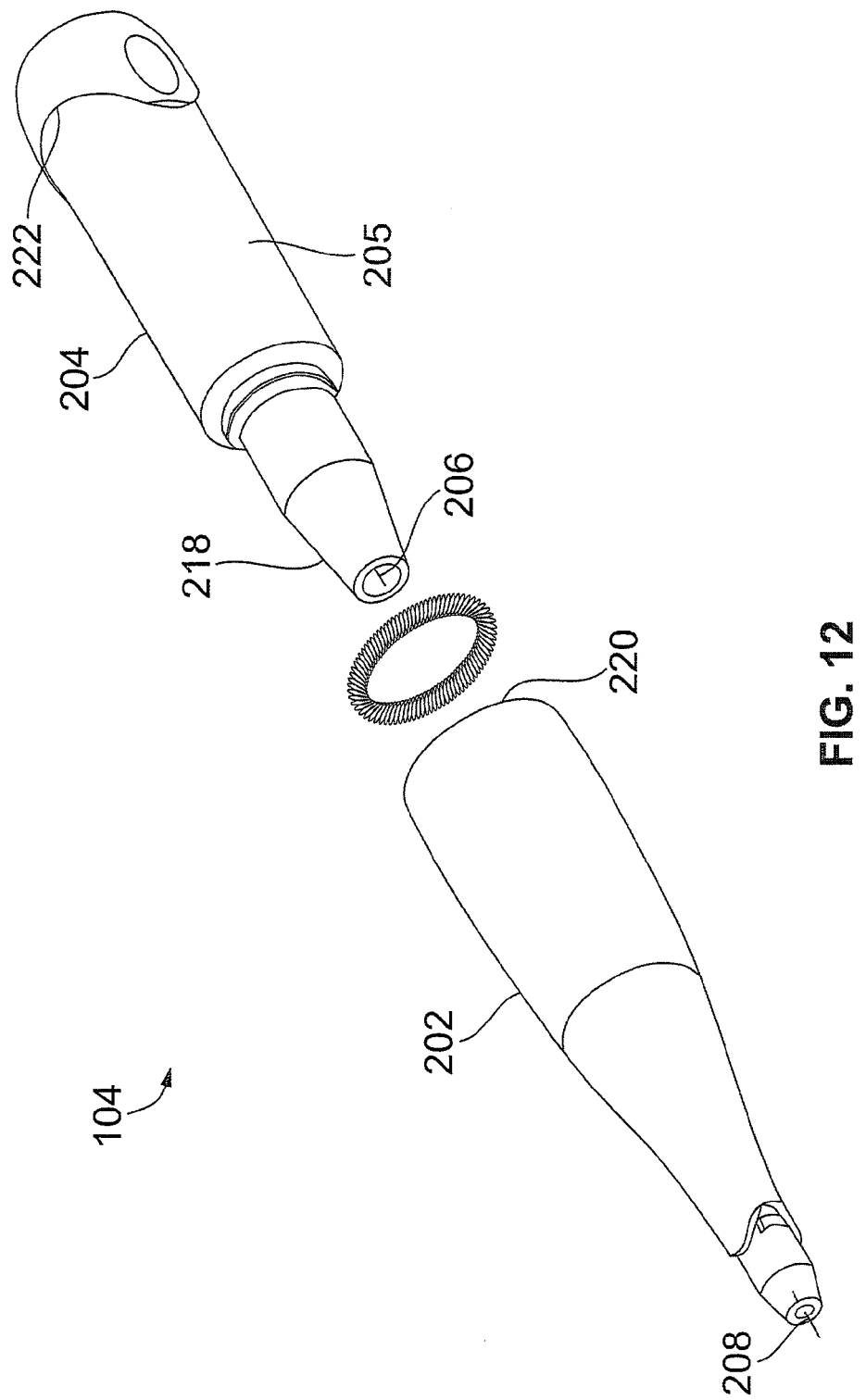
FIG. 12 shows a dental handpiece according to yet another embodiment of the disclosure.

FIG. 8 shows an exemplary embodiment of dental handpiece 104 including a first module 202 and a second module 204. First module 202 can detachably engage DPA 102 to form system 100 as shown in FIGS. 1-7. First module 202 can be an outer module configured to substantially extend around second module 204 when engaged. First module 202 can have one open end and one closed end (for example, for engaging DPA 102). First module 202 can include additional features permitting improved sterilizing and/or disinfecting. In one embodiment, first module 202 is designed to be sterilized by autoclaving. In another embodiment, first module 202 may include few or no rough areas, crevices, pockets, and the like, thereby reducing or eliminating regions for retaining contaminants or other fluids. As further described in the U.S. patent application Ser. No. 12/004,145, first module 202 may include aligment and/or keying features for detachably engaging DPA 102.

The modular nature of dental handpiece 104 permits a clinician to sterilize any one of DPA 102, first module 202, and second module 204 while still using the remaining portions of dental handpiece 104. With DPA 102, first module 202, or both being likely to be exposed to undesirable substances, second module 204 can include more expensive portions and/or portions that are more sensitive to the undesirable substances or even portions that cannot be autoclaved. To further protect second module 204 from undesirable substances, second module 204 is inserted into first module 202, which substantially covers second module 204. Upon inserting second module 204 into first module 202, a second drive 206 positioned within second module 204 detachably engages a first drive 208 positioned within first module 202. Although the exposed portion of the first drive 208 is shown in FIG. 8, as shown in FIG. 9, the first drive 208 can include features internal to the first module 202. In one embodiment, the first drive 208 is substantially impermeable to fluids thereby protecting the second module 204 and the interface between the first drive 208 and the second drive 206.

Drive 206 can be rotated by any suitable mechanism. In one embodiment, drive 206 includes a shaft rotated by a motor located in second module 204 powered by the battery (not shown) within the battery compartment (205) of second module 204. Second module 204 can be sterilized and/or disinfected by wiping with known chemical disinfectants. With first module 202 protecting second module 204, second module 204 can include additional features that may be more difficult to sterilize and/or disinfect such as the motor, electrical components, electronic components, or the like. Furthermore, second module 204 can include more expensive and delicate features because it will likely be available to the technician while the first module 202 is autoclaved.

Referring to FIGS. 8-10, second module 204 can detachably engage first module 202 through insertion and engagement of a connection mechanism 210. Connection mechanism 210 allows first module 202 and second module 204 to engage and disengage. Connection mechanism 210 is any suitable feature for detachably engaging first module 202 and second module 204. In one embodiment, connection mechanism 210 includes a first ring 212 positioned and secured (for example, by adhesive, friction, threading, flaring or other suitable securing techniques) within first module 202 and a second ring 214 positioned and secured (for example, by adhesive, friction, threading, flaring or other suitable securing techniques) within second module 204. Second ring 214 includes a gap 216. Gap 216 permits second ring 214, which is resilient, to constrict upon circumferential force being applied to second ring 214. For example, first ring 212 can have a slightly smaller interior diameter than an exterior diameter of second ring 214. With first ring 212 having a slightly smaller interior diameter than exterior diameter of second ring 214 providing an interference fit, second module 204 can be inserted into first module 202 thereby applying a circumferential force upon second ring 214. The circumferential force can constrict second ring 214 thereby permitting it to slide through first ring 212. Upon passing through first ring 212, second ring 214 can relax and secure first module 202 with second module 204. In one embodiment, upon second ring 214 sliding through first ring 212, an audible sound (for example, a clicking noise) provides confirmation that the handpiece 104 is detachably engaged. To release first module 202 from second module 204, second module 204 can be pulled from first module 202 thereby resulting in second ring 214 once again constricting. Upon second ring 214 constricting, second ring 214 can slide through first ring 212 thereby detaching first module 202 from second module 204.

In another embodiment, connection mechanism 210 may comprise one or more magnets (for example, in any combination of first module and second module 204 and/or with a ferromagnetic material such as a 400 series of stainless steel). In this embodiment, the magnets may provide a force holding first module 202 and second module 204 together. In yet another embodiment, connection mechanism 210 may be a bayonet-style connection. In yet another embodiment, connection mechanism 210 may include a canted coil spring and matching groove. In yet another embodiment, connection mechanism 210 may include an O-ring and a groove designed to be engaged by the O-ring. In yet another embodiment, connection mechanism 210 may include snap features. The snap features may be of any suitable material with some flexibility and resiliency. For example, the snap features may be plastic or metal. In yet another embodiment, connection mechanism 210 may include threading. In yet another embodiment, connection mechanism 210 may include a general interference fit. In other embodiments, connection mechanism 210 may include combinations thereof. Any suitable connection mechanism that mates and locks may be used.

Referring again to FIGS. 8-10, first module 202 and second module 204 can include alignment features for detachable engagement. Alignment features can be included on connection mechanism 210, on an interior portion of first module 202, on an exterior portion of second module, or any combination thereof. In one embodiment, an insertion portion 218 of the exterior second module 204 includes a protrusion or tongue and first module 202 includes a slot or groove for receiving the protrusion or tongue, thereby providing a tongue and groove connection. The protrusion, the slot, or both can be of any suitable shape. In a further embodiment, the shape of the protrusion provides additional alignment by increasing in width opposite the direction of insertion. Additionally or alternatively, alignment features can be included on the exterior of first module 202 and second module 204.

In one embodiment, first module 202 includes a curved feature 220 that can be received by a curved recess 222 of second module 204. Curved feature 220 and curved recess 222 align first module 202 and second module 204 during detachable engagement. Furthermore, curved feature 220 and curved recess 222 limit the orientations of detachable engagement. For example, curved feature 220 and curved recess limit detachable engagement to two orientations 180 degrees apart. In other embodiments, the alignment features may limit the orientations of detachable engagement to one orientation or more than two orientations.

Additionally or alternatively, in a non-preferred embodiment, first module 202 can be configured to receive a protective sleeve as currently described in U.S. Pat. Pub. 2009/0081610, which is incorporated by reference in its entirety, for any suitable uses described or to prevent undesirable substances from being deposited on first module 202, second module 204, or any combination thereof. The protective sleeve may be a disposable covering (for example, a flexible plastic) or reusable and able to be sterilized. However, the protective sleeve can result in additional drawbacks such as dislodging, adding cost, adding to the bulk of the dental hygiene instrument, creating waste, or some combination thereof. In another embodiment, the dental hygiene instrument 104 does not include a protective sleeve. In addition, use of the protective sleeve can increase wear associated with engagement and disengagement. Furthermore, having two openings in the protective sleeve can increase the risk of undesirable fluids entering the interior portion of the protective sleeve. In some cases, such fluids can act as an adhesive resulting in the protective sleeve becoming undesirable attached to the handpiece. In other cases, such fluids can breed infection.

While only certain features and embodiments of the invention have been shown and described, many modifications and changes may occur to those skilled in the art (for example, variations in sizes, dimensions, structures, shapes and proportions of the various elements, values of parameters (for example, temperatures, pressures, etc.), mounting arrangements, use of materials, colors, orientations, etc.) without materially departing from the novel teachings and advantages of the subject matter recited in the claims. The order or sequence of any process or method steps may be varied or re-sequenced according to alternative embodiments. It is, therefore, to be understood that the appended claims are intended to cover all such modifications and changes as fall within the true spirit of the invention. Furthermore, in an effort to provide a concise description of the exemplary embodiments, all features of an actual implementation may not have been described (i.e., those unrelated to the presently contemplated best mode of carrying out the invention, or those unrelated to enabling the claimed invention). It should be appreciated that in the development of any such actual implementation, as in any engineering or design project, numerous implementation specific decisions may be made. Such a development effort might be complex and time consuming, but would nevertheless be a routine undertaking of design, fabrication, and manufacture for those of ordinary skill having the benefit of this disclosure, without undue experimentation.

What is claimed is:

1. A cordless dental handpiece, comprising:
   a first module that includes a first drive that is configured to detachably engage a dental tool; and
   a second module configured to detachably engage the first module, the second module comprising a battery compartment;
   wherein the first module of the cordless dental handpiece is further configured to detachably engage the dental tool at a proximal end, and
   wherein the first module has a hollow distal end such that the battery compartment of the second module can be accommodated when the first module is engaged with the second module,
   the cordless dental handpiece further comprising a connection mechanism, wherein the connection mechanism comprises a first ring positioned and secured within the first module and a resilient second ring positioned and secured within the second module,
   wherein the second ring includes a gap, the gap permitting the second ring to constrict upon circumferential force being applied to the second ring by the first ring.

2. The cordless dental handpiece of claim 1, wherein the dental tool is a dental prophylaxis angle.

3. The cordless dental handpiece of claim 1, wherein a second drive positioned within the second module is configured to detachably engage the first drive positioned within the first module.

4. The cordless dental handpiece of claim 2, wherein the first drive includes a shaft rotated by a motor positioned in the second module and powered by a battery within the battery compartment.

5. The cordless dental handpiece of claim 1, further comprising an indicator positioned on the second module and powered by a battery in the battery compartment.

6. The cordless dental handpiece of claim 1, further comprising one or more contacts permitting electrical communication with the battery compartment.

7. The cordless dental handpiece of claim 6, wherein the one or more contacts are positioned on the second module and wherein detachable engagement of the first module and the second module encloses the one or more contacts, whereby the one or more contacts are protected from fluids.

8. The cordless dental handpiece of claim 1, wherein the first module is an outer module configured to extend around the second module when detachably engaged.

9. The cordless dental handpiece of claim 1, wherein the first module is configured to receive a protective sleeve.

10. The cordless dental handpiece of claim 1, wherein the cordless dental handpiece is devoid of a protective sleeve.

11. The cordless dental handpiece of claim 1, wherein an audible sound is generated upon the first module and the second module being detachably engaged.

12. The cordless dental handpiece of claim 1, wherein the first module consists of one open end.

13. The cordless dental handpiece of claim 1, wherein the dental tool is a dental bur.

14. The cordless dental handpiece of claim 1, wherein the dental tool is a dental brush.

15. A dental hygiene system, comprising:
    a dental prophylaxis angle; and
    a cordless dental handpiece, comprising:
       a first module that includes a first drive that is configured to detachably engage the dental prophylaxis angle; and
       a second module configured to detachably engage the first module, the second module comprising a battery compartment;
    wherein the first module of the cordless dental handpiece is further configured to detachably engage the dental prophylaxis angle at a proximal end, and
    wherein the first module has a hollow distal end such that the battery compartment of the second module can be accommodated when the first module is engaged with the second module,
    the cordless dental handpiece further comprising a connection mechanism, wherein the connection mechanism comprises a first ring positioned and secured within the first module and a resilient second ring positioned and secured within the second module,
    wherein the second ring includes a gap, the gap permitting the second ring to constrict upon circumferential force being applied to the second ring by the first ring.

16. A method of connecting a cordless dental handpiece, the method comprising:
    providing a cordless dental handpiece, the cordless dental handpiece comprising a first module and a second module, the first module comprising a first drive configured to detachably engage the dental prophylaxis angle at a proximal end and a hollow portion at the distal end, and the second module comprising a battery compartment, the cordless dental handpiece further comprises a connection mechanism, where the connection mechanism includes a first ring positioned and secured within the first module and a resilient second ring positioned and secured within the second module, the second ring includes a gap, the gap permitting the second ring to constrict upon circumferential force being applied to the second ring by the first ring;
    detachably engaging the first module with the second module such that the hollow portion of the first module fits over the battery compartment of the second module; and
    detachably engaging the first module of the cordless dental handpiece with a dental prophylaxis angle.

17. The method of claim 16, further comprising generating an audible sound the first module and the second module being detachably engaged.

* * * * *